US010906030B2

(12) United States Patent
Bouchy

(10) Patent No.: US 10,906,030 B2
(45) Date of Patent: Feb. 2, 2021

(54) PROCESS FOR PREPARING A CATALYST BASED ON IZM-2 FROM A SOLUTION COMPRISING SPECIFIC PRECURSORS AND USE FOR THE ISOMERIZATION OF PARAFFINIC FEEDSTOCKS

(71) Applicant: IFP Energies nouvelles, Rueil-Malmaison (FR)

(72) Inventor: Christophe Bouchy, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/212,160

(22) Filed: Dec. 6, 2018

(65) Prior Publication Data
US 2019/0168195 A1  Jun. 6, 2019

(30) Foreign Application Priority Data

Dec. 6, 2017  (FR) .................................... 17 61691

(51) Int. Cl.
| B01J 29/06 | (2006.01) |
| B01J 29/70 | (2006.01) |
| B01J 23/42 | (2006.01) |
| B01J 23/44 | (2006.01) |
| B01J 21/04 | (2006.01) |
| B01J 37/02 | (2006.01) |
| C10G 45/64 | (2006.01) |
| B01J 29/76 | (2006.01) |
| B01J 29/74 | (2006.01) |
| B01J 37/00 | (2006.01) |
| B01J 29/78 | (2006.01) |
| C07C 5/27 | (2006.01) |

(52) U.S. Cl.
CPC ............... *B01J 29/70* (2013.01); *B01J 21/04* (2013.01); *B01J 23/42* (2013.01); *B01J 23/44* (2013.01); *B01J 29/74* (2013.01); *B01J 29/76* (2013.01); *B01J 29/78* (2013.01); *B01J 37/0009* (2013.01); *B01J 37/0201* (2013.01); *B01J 37/0207* (2013.01); *B01J 37/0209* (2013.01); *B01J 37/0213* (2013.01); *C07C 5/2775* (2013.01); *C10G 45/64* (2013.01); *B01J 2229/18* (2013.01); *B01J 2229/186* (2013.01); *B01J 2229/20* (2013.01); *B01J 2229/42* (2013.01); *C07C 2529/74* (2013.01); *C07C 2529/76* (2013.01); *C07C 2529/78* (2013.01); *C10G 2300/1085* (2013.01); *C10G 2300/70* (2013.01)

(58) Field of Classification Search
CPC ............... B01J 2229/20; B01J 2229/42; B01J 2229/18; B01J 2229/186; B01J 29/74; B01J 29/76; B01J 29/78; B01J 37/0209; B01J 37/0207; B01J 37/0213; B01J 37/0201; B01J 37/0009; C07C 2529/74; C07C 2529/76; C07C 2529/78
USPC .......................... 502/60, 64, 66, 69, 74, 86
See application file for complete search history.

(56) References Cited

U.S. PATENT DOCUMENTS

| 5,178,748 A | 1/1993 | Casci et al. |
| 5,641,393 A | 6/1997 | Nakagawa |
| 8,629,073 B2 | 1/2014 | Guillon et al. |
| 9,156,748 B2 | 10/2015 | Bouchy et al. |
| 10,183,902 B2 * | 1/2019 | Bouchy ................... B01J 29/76 |
| 2011/0120910 A1 * | 5/2011 | Simon ..................... B01J 29/106 208/60 |
| 2011/0191562 A1 * | 8/2011 | Chou ....................... G06F 12/06 711/163 |
| 2013/0165730 A1 * | 6/2013 | Bouchy ................... C07C 5/226 585/739 |
| 2018/0029957 A1 * | 2/2018 | Bouchy ................... B01J 29/76 |

FOREIGN PATENT DOCUMENTS

| EP | 2607457 B1 | 6/2016 |
| WO | 10015733 A1 | 2/2010 |

OTHER PUBLICATIONS

Search Report in corresponding FR1761691 dated Jun. 30, 2018 (pp. 1-9).

* cited by examiner

*Primary Examiner* — Elizabeth D Wood
(74) *Attorney, Agent, or Firm* — Millen, White, Zelano and Branigan, P.C.

(57) ABSTRACT

The present invention relates to a process for preparing a difunctional catalyst using a zeolite IZM-2, a hydrogenating function and a matrix. The preparation process according to the invention simultaneously allows preferential localization of said hydrogenating function on the surface and/or in the microporosity of zeolite IZM-2 and homogeneous distribution of the hydrogenating function in the catalyst and preferably on zeolite IZM-2 by means of using an impregnation solution comprising specific noble metal precursors combined with the presence of ammonium salts, with a quite precise ratio of ammonium salt to noble metal.

11 Claims, 2 Drawing Sheets

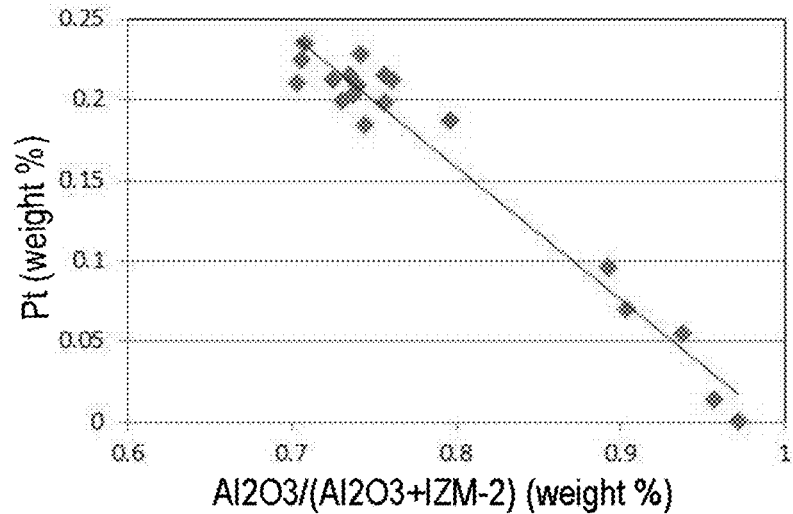
Figure 1: change in the local weight % as a function of the weight % $Al_2O_3$ /(weight % $Al_2O_3$ + weight % IZM-2) local ratio for catalyst A in accordance with the invention
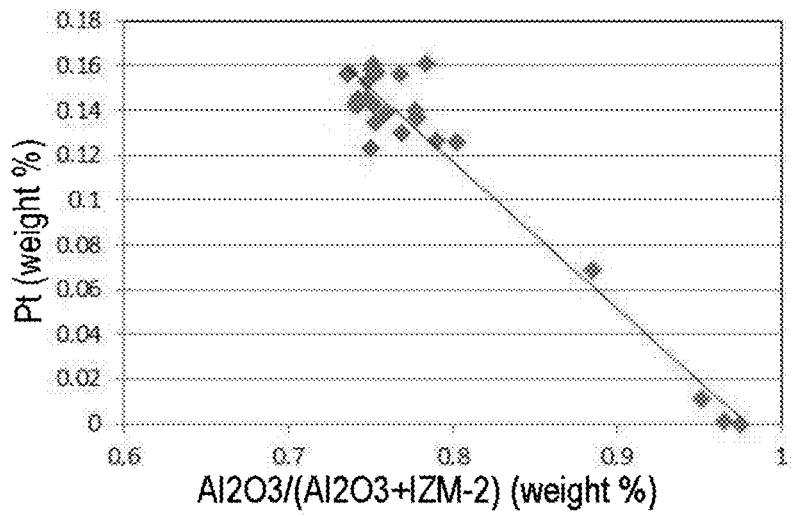
Figure 2: change in the local weight % as a function of the weight % $Al_2O_3$ /(weight % $Al_2O_3$ + weight % IZM-2) local ratio for catalyst B in accordance with the invention

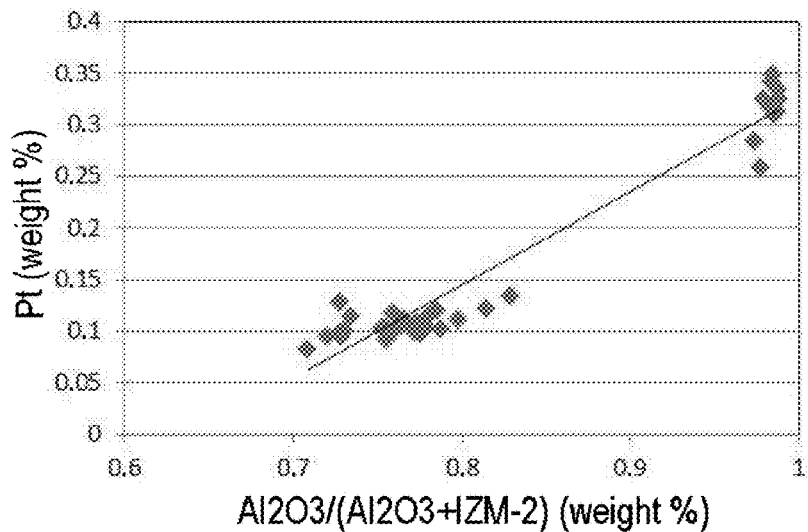
Figure 3: change in the local weight % as a function of the weight % $Al_2O_3$ /(weight % $Al_2O_3$ + weight % IZM-2) local ratio for catalyst D not in accordance with the invention
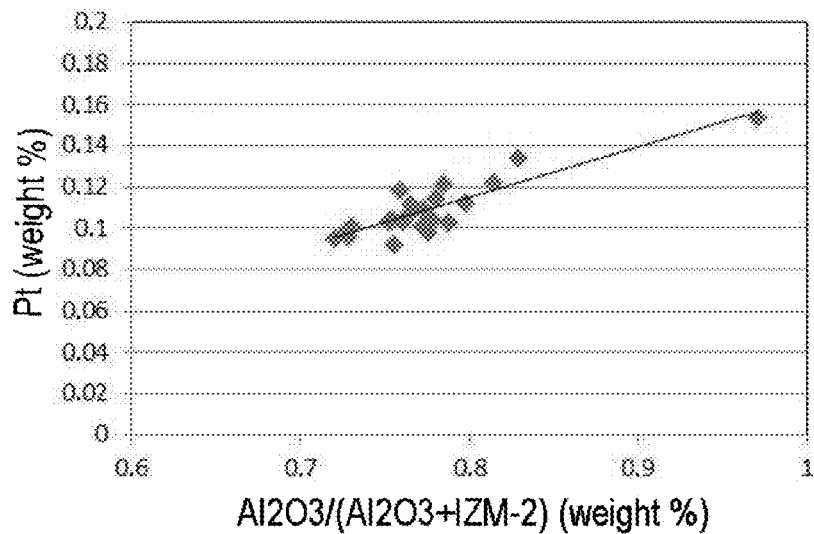
Figure 4: change in the local weight % as a function of the weight % $Al_2O_3$ /(weight % $Al_2O_3$ + weight % IZM-2) local ratio for catalyst E not in accordance with the invention

PROCESS FOR PREPARING A CATALYST BASED ON IZM-2 FROM A SOLUTION COMPRISING SPECIFIC PRECURSORS AND USE FOR THE ISOMERIZATION OF PARAFFINIC FEEDSTOCKS

PRIOR ART

In order to meet the demand for middle distillate bases, i.e. a fraction that may be incorporated into the kerosene and/or gas oil pool, various methods for producing middle distillates based on the use of petroleum, natural gas or renewable resources may be used.

Middle distillate bases may thus be produced from a paraffinic feedstock obtained from a feedstock derived from renewable sources, and in particular from vegetable oils or animal fats, which are raw or which have undergone a pretreatment, and also mixtures of such feedstocks. Specifically, said feedstocks derived from renewable sources contain chemical structures of triglyceride or free fatty acid or ester type, the structure and length of the hydrocarbon-based chain of these feedstocks being compatible with the hydrocarbons present in middle distillates. Said feedstocks derived from renewable sources produce, after hydrotreatment, paraffinic feedstocks that are free of sulfur compounds and of aromatic compounds. These paraffinic feedstocks are typically composed of linear paraffins containing between 9 and 25 carbon atoms.

Middle distillate bases may also be produced from natural gas, coal or renewable sources via the Fischer-Tropsch synthetic process. In particular, the "low-temperature" Fischer-Tropsch synthesis using cobalt catalysts makes it possible to produce essentially paraffinic linear compounds having a very variable number of carbon atoms, typically from 1 to 100 carbon atoms or even more. Separation steps may make it possible to recover paraffinic feedstocks containing between 9 and 25 carbon atoms.

However, these middle distillate bases obtained after hydrotreatment of vegetable oils or after the low-temperature Fischer-Tropsch synthetic process generally cannot be incorporated as such into the kerosene or gas oil pool in particular on account of insufficient cold properties. Specifically, high molecular weight paraffins which are linear or very sparingly branched and which are present in these middle distillate bases lead to high flow points and thus to congealing for uses at low temperature. For example, the flow point of a linear hydrocarbon containing 20 carbon atoms per molecule and whose boiling point is equal to about 340° C., i.e. typically within the middle distillate fraction, is about +37° C., which renders its use impossible, the specification being −15° C. for gas oil. In order to lower the flow point values, these linear or very sparingly branched paraffins must be totally or partially removed.

This operation may be performed by extraction with solvents such as propane or methyl ethyl ketone, this process then being referred to as deparaffinning with propane or with methyl ethyl ketone (MEK). However, these techniques are expensive, long and not always easy to perform.

Selective cracking of the longest linear paraffinic chains, which leads to the formation of compounds of lower molecular weight, part of which may be removed by distillation, constitutes a solution for reducing the flow point values. Given their shape selectivity, zeolites are among the catalysts most widely used for this type of process. The catalyst that is the most widely used in the deparaffinning category by selective cracking is zeolite ZSM-5, of MFI structural type, which has three-dimensional porosity, with medium pores (aperture at 10 oxygen atoms 10MR). However, the cracking brought about in such processes leads to the formation of large amounts of products of lower molecular weights, such as butane, propane, ethane and methane, which considerably reduces the yield of desired products.

Another solution for improving the cold resistance consists in isomerizing long linear paraffins while minimizing the cracking. This may be achieved by performing a hydroisomerization process using difunctional catalysts. The difunctional catalysts involve a Brønsted acid phase (for example a zeolite) and a hydro/dehydrogenating phase (for example platinum) and generally a matrix (for example alumina). The appropriate choice of the acidic phase makes it possible to promote the isomerization of long linear paraffins and to minimize the cracking. Thus, the form selectivity of medium-pore (10MR) one-dimensional zeolites such as zeolites ZSM-22, ZSM-23, NU-10, ZSM-48 and ZBM-30 makes them particularly suitable for use for obtaining catalysts that are selective towards isomerization.

Recently, the Applicant has also discovered that the use of zeolite IZM-2 is also suitable for obtaining catalysts that are selective towards the isomerization of long paraffins.

However, it is well known that factors other than the acidic phase have an impact on the activity and selectivity of a difunctional catalyst. Hydroisomerization and hydrocracking of normal paraffins have thus been the subject of numerous academic studies since the original investigations in the 1960s by Weisz or Coonradt and Garwood. The most commonly accepted mechanism first involves dehydrogenation of the n-paraffin to an n-olefin on the hydro-dehydrogenating phase and then, after diffusion to the acidic phase, protonation to a carbenium ion. After structural rearrangement and/or $\beta$-cleavage, the carbenium ions are desorbed from the acidic phase in the form of olefins after deprotonation. Next, after diffusion to the hydro-dehydrogenating phase, the olefins are hydrogenated to form the final reaction products. When maximum selectivity towards isomerization is desired, the cracking reactions on the acidic phase should be limited. It is then appropriate to have a hydro/dehydrogenating function that is sufficiently active with respect to the acid function so as to rapidly hydrogenate the olefinic intermediates. When the overall reaction rate is only controlled by the steps catalysed by the acid function, the difunctional catalyst is said to be "ideal".

The proximity between the two functions on the catalyst may also have an impact on the performance of the difunctional catalyst. Thus, Zecevic et al. (Nature, 2015, 528, 245-254) recently studied the impact of the localization of platinum on the hydroisomerization performance of long paraffins (n-decane, n-nonadecane, pristane) by a difunctional catalyst using the zeolite USY as acidic phase and an alumina matrix. It is observed that the difunctional catalyst for which platinum is deposited on alumina is systematically more selective towards isomerization than the catalyst for which platinum is deposited in the zeolite. In the light of these results, a person skilled in the art is thus inclined to favour localization of the hydrogenating function on the alumina matrix rather than on the acidic phase to improve the selectivity towards isomerization. From the point of view of the activity, localizing platinum on the alumina matrix has a variable impact depending on the long paraffin under consideration: a positive impact as regards n-decane, a marginal impact as regards n-nonadecane and finally a negative impact as regards pristane.

During its investigations performed to improve the selectivity towards isomerization of long paraffins and the activity of difunctional catalysts using zeolite IZM-2 as acid function, the Applicant has discovered a surprising impact of the localization of the hydro/dehydrogenating function combined with the distribution of said function on the performance of the difunctional catalyst.

Thus, the present invention relates to a process for preparing a difunctional catalyst using a zeolite IZM-2, a hydrogenating function and a matrix. The preparation process according to the invention simultaneously allows preferential localization of said hydrogenating function on the surface and/or in the microporosity of zeolite IZM-2 and homogeneous distribution of the hydrogenating function in the catalyst and preferably on zeolite IZM-2 by means of using an impregnating solution comprising specific noble metal precursors combined with the presence of ammonium salts, with a quite precise ratio of ammonium salt to noble metal.

Another subject of the present invention relates to the catalyst obtained via said process.

Another subject of the present invention relates to a process for the isomerization of paraffinic feedstocks derived from hydrotreated vegetable oils and/or animal oils or from low-temperature Fischer-Tropsch synthesis, said process using said difunctional catalyst.

Surprisingly, preferential localization of the hydrogenating function comprising at least one noble metal from group VIII and preferably platinum on the surface and/or in the microporosity of zeolite IZM-2 makes it possible to obtain a catalyst that is more selective towards the isomerization reaction than when said function is preferentially deposited on the alumina matrix. Moreover, when said hydrogenating function is preferentially deposited on and/or in the microporosity of zeolite IZM-2 and furthermore homogeneously distributed within the catalyst, the activity of the catalyst is thereby improved.

SUMMARY OF THE INVENTION

The present invention relates to a process for preparing a difunctional catalyst comprising an acid function constituted by zeolite IZM-2, a hydrogenating function comprising at least one noble metal from group VIII of the Periodic Table, chosen from platinum and palladium, and a matrix, said process comprising at least the following steps:
  i) a step of preparing the support for the catalyst by forming zeolite IZM-2 with a matrix such that the weight percentage of zeolite is advantageously between 1% and 50% relative to the weight of the support,
  ii) a step of depositing at least one noble metal from group VIII of the Periodic Table by impregnation of the support prepared in step i) with an aqueous solution comprising at least the following compounds:
    at least one ammoniacal compound chosen from the platinum(II) tetramine salts of formula $Pt(NH_3)_4(OH)_2$, $Pt(NH_3)_4(NO_3)_2$ or $Pt(NH_3)_4X_2$, the platinum (IV) hexamine salts of formula $Pt(NH_3)_6X_4$; the platinum(IV) halopentamine salts of formula $(PtX(NH_3)_5)X_3$; the platinum N-tetrahalodiamine salts of formula $PtX_4(NH_3)_2$; and the halogenated compounds of formula $H(Pt(acac)_2X)$; the palladium(II) salts $Pd(NH_3)_4SO_4$ or $Pd(NH_3)_4X_2$, in which X is a halogen chosen from chlorine, fluorine, bromine and iodine, X preferably being chlorine, and "acac" represents the acetylacetone group (of empirical formula $C_5H_7O_2$), an acetylacetone derivative,
    and at least one ammonium salt chosen from ammonium nitrate $NH_4NO_3$, ammonium chloride $NH_4Cl$, ammonium hydroxide $NH_4OH$, ammonium bicarbonate $NH_4HCO_3$ and ammonium acetate $NH_4H_3C_2O_2$, alone or as a mixture,
      the mole ratio between the ammonium salt and the noble metal being between 0.1 and 400.

An advantage of the present invention is that it provides a process for preparing a difunctional catalyst comprising an acidic phase based on zeolite IZM-2 and a hydrogenating function based on noble metals from group VIII, which, by means of using an impregnation solution comprising specific noble metal precursors combined with the presence of ammonium salts, with a quite precise ratio of ammonium salt to noble metal, makes it possible to obtain both preferential localization of said hydrogenating function on the surface and/or in the microporosity of zeolite IZM-2 and homogeneous distribution of the hydrogenating function in the catalyst.

An advantage of the present invention is that it provides a catalyst obtained via said process, said catalyst being characterized by preferential localization of said hydrogenating function on the surface and/or in the microporosity of zeolite IZM-2 and homogeneous distribution of the hydrogenating function in the catalyst.

Another advantage of the present invention is that it provides a process for the isomerization of paraffinic feedstocks derived from hydrotreated vegetable oils and/or animal oils or from low-temperature Fischer-Tropsch synthesis using said difunctional catalyst thus obtained, firstly allowing better selectivity towards middle distillates by means of localization of the hydrogenating function on the surface and/or in the microporosity of zeolite IZM-2, and also better activity, in the case where, in addition to being localized preferentially on zeolite IZM-2, the hydrogenating function is also homogeneously distributed on said catalyst.

DETAILED DESCRIPTION OF THE INVENTION

In accordance with the invention, the present invention relates to a process for preparing a difunctional catalyst comprising an acid function constituted by zeolite IZM-2, a hydrogenating function comprising at least one noble metal from group VIII of the Periodic Table, chosen from platinum and palladium alone or as a mixture, and a matrix.

The catalyst prepared according to the invention comprises zeolite IZM-2 which constitutes the acid function of said catalyst. Zeolite IZM-2 has a crystalline structure.

Zeolite IZM-2 is a crystalline microporous solid having a crystalline structure described in patent application FR 2 918 050. The process for preparing zeolite IZM-2 is also described in said patent application.

Said solid IZM-2 has a chemical composition expressed on an anhydrous basis, in terms of moles of oxides, defined by the following general formula: $XO_2:aY_2O_3:bM_2/nO$, in which X represents at least one tetravalent element, Y represents at least one trivalent element and M is at least one alkali metal and/or alkaline-earth metal of valency n.

X is preferentially chosen from silicon, germanium, titanium and a mixture of at least two of these tetravalent elements; very preferentially, X is silicon and Y is preferentially chosen from aluminium, boron, iron, indium and gallium; very preferentially, Y is aluminium. M is preferentially chosen from lithium, sodium, potassium, calcium, magnesium and a mixture of at least two of these metals, and very preferentially M is sodium. Preferably, X represents silicon, the crystalline solid IZM-2 according to the invention is then an entirely silicic solid when the element Y is absent from the composition of said solid IZM-2. It is also advantageous to use as element X a mixture of several elements X, in particular a mixture of silicon with another element X chosen from germanium and titanium, preferably germanium. Thus, when silicon is present as a mixture with another element X, the crystalline solid IZM-2 according to the invention is then a crystalline metallosilicate having an x-ray diffraction diagram identical to that described in table 1 when it is in its calcined form. Even more preferably and in the presence of an element Y, X being silicon and Y being aluminium: the crystalline solid IZM-2 according to the invention is then an aluminosilicate.

Preferably, zeolite IZM-2 is in aluminosilicate form.

Preferably, the mole ratio of the number of silicon atoms to the number of aluminium atoms Si/Al is less than 200, preferably less than 150 and very preferably less than 120.

The zeolite IZM-2 included in the composition of the support for the catalyst prepared according to the invention is advantageously exchanged via at least one treatment with a solution of at least one ammonium salt so as to obtain the ammonium form of zeolite IZM-2, which, once calcined, leads to the acid form (H+) of said zeolite IZM-2. This exchange step may be performed at any step in the preparation of the catalyst, i.e. after the step of preparing zeolite IZM-2, after the step of forming zeolite IZM-2 with a matrix, or even after the step of introducing the hydro-dehydrogenating metal.

Said zeolite IZM-2 included in the composition of the support for the catalyst used in the process according to the invention is advantageously at least partly, and preferably virtually totally, in acid form, i.e. in acid form (H+).

According to the invention, the catalyst prepared comprises at least one matrix. Said matrix may advantageously be amorphous or crystalline.

Preferably, said matrix is advantageously chosen from the group formed by alumina, silica, silica-alumina, clays, titanium oxide, boron oxide and zirconia, taken alone or as a mixture, or else aluminates may also be chosen. Preferably, alumina is used as matrix. Preferably, said matrix contains alumina in all its forms known to those skilled in the art, for instance aluminas of alpha, gamma, eta and delta type. Said aluminas differ in their specific surface area and their pore volume.

The mixture of the matrix and of zeolite IZM-2 formed constitutes the support for the catalyst.

Step i)

In accordance with the invention, the process comprises a step i) of preparing the support for the catalyst by forming zeolite IZM-2 with a matrix such that the weight percentage of zeolite is advantageously between 1% and 50% relative to the weight of the support.

Forming

The support for the catalyst used in the process according to the invention may advantageously be formed via any technique known to those skilled in the art. The forming may advantageously be performed, for example, by extrusion, by pelletizing, by the drop coagulation (oil-drop) method, by granulation on a rotating plate or via any other method that is well known to those skilled in the art. The supports thus obtained may be in various shapes and sizes. Preferably, step i) is performed by blending-extrusion.

During the forming of the support by blending and then extrusion, said zeolite IZM-2 may be introduced during the dissolution or suspension of the alumina compounds or alumina precursors, for instance boehmite. Said zeolite IZM-2 may be, for example, without this being limiting, in the form of a powder, a ground powder, a suspension, or a suspension which has undergone a deagglomeration treatment. Thus, for example, said zeolite may advantageously be placed in acidified or non-acidified suspension at a concentration adjusted to the final IZM-2 content targeted in the catalyst according to the invention. This suspension commonly referred to as a slip is then mixed with the alumina compounds or alumina precursors.

Moreover, the use of additives may advantageously be performed to facilitate the forming and/or to improve the final mechanical properties of the supports, as is well known to those skilled in the art. Examples of additives that may especially be mentioned include cellulose, carboxymethylcellulose, carboxyethylcellulose, tall oil, xanthan gums, surfactants, flocculants such as polyacrylamides, carbon black, starches, stearic acid, polyacryl alcohol, polyvinyl alcohol, biopolymers, glucose, polyethylene glycols, etc.

Water may advantageously be added or removed to adjust the viscosity of the paste to be extruded. This step may advantageously be performed at any stage in the blending step.

To adjust the solids content of the paste to be extruded so as to make it extrudable, a compound that is predominantly solid, preferably an oxide or a hydrate, may also be added. A hydrate is preferably used, and even more preferably an aluminium hydrate. The loss on ignition of this hydrate is advantageously greater than 15%.

Extrusion of the paste derived from the blending step may advantageously be performed with any conventional commercially available tool. The paste derived from the blending is advantageously extruded through a die, for example using a piston or a single-screw or twin-screw extruder. The extrusion may advantageously be performed via any method known to those skilled in the art.

The catalyst supports prepared in step i) according to the invention are generally in the form of cylindrical extrudates or polylobal extrudates such as bilobal, trilobal or polylobal extrudates of straight or twisted form, but may optionally be manufactured and used in the form of crushed powders, lozenges, rings, beads and/or wheels. Preferably, the catalyst supports according to the invention are in the form of spheres or extrudates. Advantageously, the support is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used.

Drying

The support thus obtained on conclusion of the forming step i) may then advantageously be subjected to a drying step. Said drying step is advantageously performed via any technique known to those skilled in the art.

Preferably, the drying is performed under a flow of air. Said drying may also be performed under a flow of any oxidizing, reducing or inert gas. Preferably, the drying is advantageously performed at a temperature of between 50 and 180° C., preferably between 60 and 150° C. and very preferably between 80 and 130° C.

Calcination

Said support, optionally dried, then preferably undergoes a calcination step.

Said calcination step is advantageously performed in the presence of molecular oxygen, for example by flushing with air, at a temperature advantageously greater than 200° C. and less than or equal to 1100° C. Said calcination step may advantageously be performed in a traversed bed, in a licked bed or under a static atmosphere. For example, the oven used may be a rotary oven or may be a vertical oven with radial cross layers. Preferably, said calcination step is performed for between more than one hour at 200° C. and less than one hour at 1100° C. For the formed and optionally dried support, the calcination may advantageously be performed in the presence of water vapour and/or in the presence of an acidic or basic vapour. For example, the calcination may be performed under a partial pressure of ammonia.

Post-Calcination Treatments

Post-calcination treatments may optionally be performed, so as to improve the properties of the calcined support, especially the textural properties.

Thus, the catalyst support used in the process according to the present invention may be subjected to a hydrothermal treatment in a confined atmosphere. The term "hydrothermal treatment in a confined atmosphere" means a treatment in an autoclave in the presence of water at a temperature above room temperature, preferably above 25° C., preferably above 30° C.

In the course of this hydrothermal treatment, the support may advantageously be impregnated, prior to its treatment in the autoclave (the autoclaving being done either in the vapour phase or in the liquid phase, this vapour or liquid phase of the autoclave possibly being acidic or not). This impregnation, prior to autoclaving, may advantageously be acidic or not. This impregnation, prior to autoclaving, may advantageously be performed dry or by immersing the support in an acidic aqueous solution. The term "dry impregnation" means placing the support in contact with a volume of solution less than or equal to the total pore volume of the support. Preferably, the impregnation is performed dry. The autoclave is preferably a rotating-basket autoclave such as the one defined in patent application EP 0 387 109 A. The temperature during the autoclaving may be between 100 and 250° C. for a period of time of between 30 minutes and 3 hours.

Step ii): Deposition of the Hydro-Dehydrogenating Function

In accordance with the invention, the deposition of the hydro-dehydrogenating function is performed after the forming step i).

In accordance with the invention, the process comprises a step ii) of depositing at least one noble metal from group VIII of the Periodic Table by impregnating the support prepared in step i), which has optionally undergone a drying and/or calcination and/or post-calcination treatment step, with an aqueous solution comprising at least the following compounds:

at least one ammoniacal compound chosen from the platinum(II) tetramine salts of formula $Pt(NH_3)_4(OH)_2$, $Pt(NH_3)_4(NO_3)_2$ or $Pt(NH_3)_4X_2$, the platinum(IV) hexamine salts of formula $Pt(NH_3)_6X_4$; the platinum(IV) halopentamine salts of formula $(PtX(NH_3)_5)X_3$; the platinum N-tetrahalodiamine salts of formula $PtX_4(NH_3)_2$; and the halogenated compounds of formula $H(Pt(acac)_2X)$; the palladium(II) salts $Pd(NH_3)_4SO_4$ or $Pd(NH_3)_4X_2$, in which X is a halogen chosen from chlorine, fluorine, bromine and iodine, X preferably being chlorine, and "acac" represents the acetylacetonate group (of empirical formula $C_5H_7O_2$), an acetylacetone derivative, and at least one ammonium salt chosen from ammonium nitrate $NH_4NO_3$, ammonium chloride $NH_4Cl$, ammonium hydroxide $NH_4OH$, ammonium bicarbonate $NH_4HCO_3$ and ammonium acetate $NH_4H_3C_2O_2$, alone or as a mixture, the mole ratio between the ammonium salt and the noble metal being between 0.1 and 400.

The hydro-dehydrogenating function may advantageously be introduced before or after calcination of the support, preferably after.

In accordance with the invention, the support is impregnated with an aqueous solution. The impregnation of the support is preferably performed via the method of "dry" impregnation or excess impregnation of a solution, which are well known to those skilled in the art. The impregnation may advantageously be performed in a single step with a solution containing all of the constituent elements of the final catalyst.

Preferably, deposition by excess impregnation is used, under the following conditions:

filling of the pore volume of the support to be impregnated with distilled water and maturing for at least 30 minutes;

placing the support in contact with the impregnation solution, the ratio of the volume of solution to the mass of support being between 2 and 150 ml of solution per gram of support, preferably between 4 and 100 ml and very preferably between 5 and 80 ml, for a time of between 5 minutes and 48 hours, preferably between 15 minutes and 36 hours and very preferably between 30 minutes and 24 hours, at a temperature of between 10 and 95° C., preferably between 15 and 90° C. and very preferably between 20 and 85° C.

Implementation of step ii) by impregnating the support with an aqueous solution comprising the specific ammoniacal metal salts as claimed allows the production of a difunctional catalyst comprising an acidic phase based on zeolite IZM-2 and a hydrogenating function based on noble metals from group VIII in which the group VIII metal is located on the outer surface of the zeolite IZM-2 crystals and/or in the microporosity of the zeolite IZM-2, i.e. in the zeolite IZM-2 crystals.

In accordance with the invention, the difunctional catalyst prepared according to the invention comprises at least one noble metal from group VIII chosen from platinum and palladium, alone or as a mixture, and very preferably platinum is chosen.

Preferably, step ii) consists in depositing at least one noble metal, preferably platinum, by impregnating the support prepared in step i) with an aqueous solution comprising ammoniacal compounds chosen from the platinum(II) tetramine salts of formula $Pt(NH_3)_4(OH)_2$, $Pt(NH_3)_4(NO_3)$ or $Pt(NH_3)_4X_2$, the platinum(IV) hexamine salts of formula $Pt(NH_3)_6X_4$; the platinum(IV) halopentamine salts of formula $(PtX(NH_3)_5)X_3$; the platinum N-tetrahalodiamine salts of formula $PtX_4(NH_3)_2$; and the halogenated compounds of formula $H(Pt(acac)_2X)$; X and "acac" having the abovementioned meaning, and preferably from the platinum(II) tetramine salts of formula $Pt(NH_3)_4(OH)_2$, $Pt(NH_3)_4(NO_3)$, or $Pt(NH_3)_4X_2$.

Preferably, said step ii) is performed so as to deposit on said support a content of noble metal and preferably of platinum of between 0.01% and 4% and preferably between 0.05% and 2% by weight relative to the total mass of said catalyst.

The preferential localization of the noble metal from group VIII in the crystals and/or on the outer surface of the crystals of zeolite IZM-2 may be demonstrated with a Castaing microprobe. A few extrudates are coated with resin (Struers, Ballerup) and then polished and metallized with carbon. The sample is then introduced into a Jeol JXA8100 machine to analyse at various points the local composition of silicon, aluminium and platinum. Starting with the local composition of aluminium and silicon, and knowing the silicon composition of the zeolite, the alumina/(IZM-2+alumina) mass ratio may be deduced for each point analysed. The change in the local composition of platinum as a function of the alumina/(IZM-2+alumina) local mass ratio can thus be plotted and the preferential localization of platinum on the alumina or on the zeolite can be checked. When the local composition of platinum increases as the alumina/(IZM-2+alumina) local mass ratio increases, then the platinum is preferentially located on the alumina. When the local composition of platinum decreases as the alumina/(IZM-2+alumina) local mass ratio increases, then the platinum is preferentially located on the zeolite.

In accordance with the invention, the impregnation solution also contains at least one ammonium salt not containing any noble metals, chosen from ammonium nitrate $NH_4NO_3$, ammonium chloride $NH_4Cl$, ammonium hydroxide $NH_4OH$, ammonium bicarbonate $NH_4HCO_3$ and ammonium acetate $NH_4H_3C_2O_2$, alone or as a mixture, and preferably from ammonium nitrate $NH_4NO_3$, ammonium chloride $NH_4Cl$ and ammonium acetate $NH_4H_3C_2O_2$, alone or as a mixture.

According to the invention, the concentrations of the various species in solution are such that the mole ratio between the ammonium salt and the noble metal is between 0.1 and 400, preferably between 0.2 and 200 and very preferably between 0.3 and 150.

The mole ratio between the ammonium salt and the platinum is chosen so as to obtain a homogeneous distribution of the noble metal and preferably of the platinum in the catalyst and preferably on the zeolite IZM-2.

The platinum concentrations in the impregnation solution are adjusted so as to obtain the desired content of noble metal in the final catalyst.

Thus, according to the invention, the impregnation solution contains both the compounds containing the specific noble metal precursors and ammonium salts not containing any noble metals in the proportions as claimed. This allows both preferential localization of said hydrogenating function on the surface and/or in the microporosity of the zeolite IZM-2 and homogeneous distribution of the hydrogenating function in the catalyst and preferably on the zeolite.

The Castaing microprobe makes it possible to check whether an element, in the present case platinum, is homogeneously distributed in the catalyst via calculation of a distribution coefficient (cf. L. Sorbier, Determining the Distribution of Metal by Electron Probe Micro Analysis, in: H. Toulhoat, P. Raybaud (Eds.), Catalysis by Transition Metal Sulphides, Ed. Technip, Paris, 2013, pages 407-411 and cited references). The macroscopic distribution coefficient for platinum, obtained from its profile determined with a Castaing microprobe, defined as the ratio of the platinum concentrations at the core of the extrudate relative to at the edge of this same extrudate, is between 0.7 and 1.3 and preferably between 0.8 and 1.2.

The value of this ratio, in the region of 1, is evidence of the homogeneity of distribution of the platinum in the catalyst.

The dispersion of the noble metal(s) from group VIII, determined by chemisorption, for example by $H_2/O_2$ titration or by carbon monoxide chemisorption, is between 10% and 100%, preferably between 20% and 100% and more preferably between 30% and 100%.

In one embodiment, the aqueous solution from step ii) or an aqueous solution different from that of step ii) may also comprise the precursors of the metals from groups IIIA, IVA and VIIB of the Periodic Table of the Elements, preferably chosen from gallium, indium, tin and rhenium and preferably chosen from indium, tin and rhenium. All the precursors of such metals may be suitable for use.

In the case where a solution different from that of step ii) is used, the depositions of the various elements are performed successively.

According to one variant, said precursors of said metals may be impregnated on the support derived from step i) separately from the precursors of the noble metals from group VIII.

When at least one metal from groups IIIA, IVA and VIIB is added separately, it is preferable for it to be added after the metal from group VIII. In this case, a second optional step of impregnation of at least one aqueous solution comprising the precursors of the metals from groups IIIA, IVA and VIIB may advantageously be performed after step ii).

The additional metal chosen from the metals of groups IIIA, IVA and VIIB may be introduced by means of an aqueous solution comprising compounds chosen from chlorides, bromides and nitrates of the metals from groups IIIA, IVA and VIIB. For example, in the case of indium, the nitrate or the chloride is advantageously used, and, in the case of rhenium, perrhenic acid is advantageously used. The additional metal chosen from the metals of groups IIIA, IVA and VIIB may also be introduced via a solution comprising at least one organic compound chosen from the group constituted by complexes of said metal, and preferably polyketone complexes of the metal and hydrocarbylmetals chosen from alkyl, cycloalkyl, aryl, alkylaryl and arylalkyl metals. In the latter case, the introduction of the metal is advantageously performed using a solution of the organometallic compound of said metal in an organic solvent. Organohalogen compounds of the metal may also be used. Organic compounds of metals that may be mentioned in particular include tetrabutyltin, in the case of tin, and triphenylindium, in the case of indium.

If the additional metal chosen from the metals of groups IIIA, IVA and VIIB is introduced before the metal from group VIII, the compound of the IIIA, IVA and/or VIIB metal used is generally chosen from the group constituted by the halide, nitrate, acetate, tartrate, carbonate and oxalate of the metal. The introduction is then advantageously performed in an aqueous solution comprising said compounds. However, it may also be introduced using a solution of an organometallic compound of the metal, for example tetrabutyltin. In this case, before introducing at least one metal from group VIII, calcination in air will be performed.

Preferably, the deposition(s) are performed so as to deposit on said support a content of metals from groups IIIA, IVA and VIIB of between 0.01% and 2% and preferably between 0.05% and 1% by weight relative to the total mass of said catalyst.

At least one drying step may advantageously be performed after the impregnation step(s), and preferably after step ii). Said drying step is advantageously performed via any technique known to those skilled in the art.

Preferably, the drying is performed under a flow of air. Said drying may also be performed under a flow of any oxidizing, reducing or inert gas. Preferably, the drying is advantageously performed at a temperature of between 50 and 180° C., preferably between 60 and 150° C. and very preferably between 80 and 130° C.

At least one calcination step may advantageously be performed after the impregnation step(s), and preferably after step ii) and preferably after at least one drying step.

Said calcination step is advantageously performed in the presence of molecular oxygen, for example by flushing with air, at a temperature advantageously greater than 200° C. and less than or equal to 1100° C. Said calcination step may advantageously be performed in a traversed bed, in a licked bed or under a static atmosphere. For example, the oven used may be a rotary oven or may be a vertical oven with radial cross layers. Preferably, said calcination step is performed for between more than one hour at 200° C. and less than one hour at 1100° C.

In the case where several successive impregnation steps are performed, intermediate drying and/or calcination steps and/or a reduction step may advantageously be performed between the successive steps of impregnation with the various metals.

Before its use in the process according to the invention, the catalyst obtained on conclusion of the preparation process according to the invention is preferably subjected to a reduction step. This reduction step is advantageously performed by treatment under hydrogen at a temperature of between 150° C. and 650° C. at a total pressure of between 0.1 and 25 MPa. For example, a reduction consists of a stage at 150° C. for two hours and then a temperature increase up to 450° C. at a rate of 1° C./minute, and then a stage of two hours at 450° C.; throughout this reduction step, the hydrogen flow rate is 1000 normal $m^3$ of hydrogen per tonne of catalyst and the total pressure is kept constant at 0.2 MPa. Any ex-situ reduction method may advantageously be envisaged. Prior reduction of the final catalyst ex-situ, under a stream of hydrogen, may be performed, for example at a temperature of from 450° C. to 600° C., for a time of from 0.5 to 4 hours.

Said catalyst also advantageously comprises sulfur. In the case where the catalyst of the invention contains sulfur, said sulfur may be introduced at any step in the preparation of the catalyst: before or after the forming and/or drying and/or calcination step, before and/or after the introduction of the metal(s) mentioned previously, or alternatively by in-situ and/or ex-situ sulfurization before the catalytic reaction. In the case of in-situ sulfurization, the reduction, if the catalyst has not been reduced beforehand, takes place before the sulfurization. In the case of ex-situ sulfurization, the reduction is also performed, followed by sulfurization. The sulfurization is preferably performed in the presence of hydrogen using any sulfurizing agent that is well known to those skilled in the art, for instance dimethyl sulfide or hydrogen sulfide.

The catalysts according to the invention are in various shapes and sizes. They are generally used in the form of cylindrical extrudates and/or polylobal extrudates such as bilobal, trilobal or polylobal extrudates of straight and/or twisted form, but may optionally be manufactured and used in the form of crushed powders, lozenges, rings, beads and/or wheels. Preferably, the catalysts used in the process according to the invention are in the form of spheres or extrudates. Advantageously, the catalyst is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used. The metal deposit does not change the form of the support.

The preparation process according to the invention thus makes it possible to obtain a difunctional catalyst comprising an acidic phase based on zeolite IZM-2 and a hydrogenating function based on noble metals from group VIII allowing both preferential localization of said hydrogenating function on the surface and/or in the microporosity of the zeolite IZM-2 and homogeneous distribution of the hydrogenating function on said catalyst.

Another subject of the invention relates to the catalyst comprising an acid function constituted by zeolite IZM-2, a hydrogenating function comprising at least one noble metal from group VIII of the Periodic Table chosen from platinum and palladium, and a matrix, obtained via the process according to the invention.

In accordance with the invention, the metal from group VIII is preferentially localized in the crystals and/or at the surface of the crystals of the zeolite IZM-2 and the metal from group VIII is homogeneously distributed on said catalyst.

Said catalyst prepared according to the invention may advantageously comprise at least one additional metal chosen from the group formed by metals from groups IIIA, IVA and VIIB of the Periodic Table of the Elements, preferably chosen from gallium, indium, tin and rhenium. Said additional metal is preferably chosen from indium, tin and rhenium.

Said catalyst also advantageously comprises sulfur.

Said catalyst prepared according to the invention more particularly comprises, and preferably is constituted of:
from 1% to 50%, preferably from 2% to 45% and even more preferably from 3% to 40% by weight of zeolite IZM-2 according to the invention,
from 0.01% to 4% and preferably from 0.05% to 2% by weight of at least one metal from group VIII of the Periodic Table of the Elements, preferably platinum,
optionally from 0.01% to 2% and preferably from 0.05% to 1% by weight of at least one additional metal chosen from the group formed by metals from groups IIIA, IVA and VIIB,
optionally a sulfur content, preferably such that the ratio of the number of moles of sulfur to the number of moles of the metal(s) from group VIII is between 0.3 and 20,
at least one matrix, preferably alumina, providing the remainder to 100% in the catalyst.

The Isomerization Process

A subject of the present invention is also a process for the isomerization of a paraffinic feedstock, said process comprising placing said paraffinic feedstock in contact with at least said catalyst according to the invention present in a catalytic reactor.

In accordance with the invention, said paraffinic feedstock used in the process according to the invention is produced from renewable resources.

The paraffins of said paraffinic feedstock contain between 9 and 25 carbon atoms, preferably between 10 and 25 and very preferably between 10 and 22. The paraffin content in said feedstock used in the process according to the invention is advantageously greater than 90% by weight, preferably greater than 95% by weight and even more preferably greater than 98% by weight. Within said paraffins, the mass content of isoparaffins is less than 15%, preferably less than 10% and very preferably less than 5%.

Preferably, said paraffinic feedstock is produced from renewable resources chosen from vegetable oils, oils from algae or algal oils, fish oils and fats of vegetable or animal origin, or mixtures of such feedstocks.

Said vegetable oils may advantageously be totally or partly raw or refined, and derived from plants chosen from rapeseed, sunflower, soybean, palm, olive, coconut, coconut kernel, castor oil plant, cotton, groundnut oil, linseed oil and sea kale oil, and all oils derived, for example, from sunflower or from rapeseed by genetic modification or hybridization, this list not being limiting. Said animal fats are advantageously chosen from blubber and fats composed of residues from the food industry or derived from the catering industries. Frying oils, various animal oils such as fish oils, tallow and lard may also be used.

The renewable resources from which is produced the paraffinic feedstock used in the process according to the invention essentially contain chemical structures of triglyceride type which a person skilled in the art also knows by the name fatty acid triester, and also free fatty acids, the fatty chains of which contain between 9 and 25 carbon atoms.

The hydrocarbon chain structure and length of these fatty acid compounds is compatible with the hydrocarbons present in gas oil and kerosene, i.e. the middle distillate fraction. A fatty acid triester is thus composed of three fatty acid chains. These fatty acid chains in triester form or in free fatty acid form have a number of unsaturations per chain, also known as the number of carbon-carbon double bonds per chain, generally between 0 and 3, but which may be higher in particular for oils derived from algae which generally have from 5 to 6 unsaturations per chain.

The molecules present in said renewable resources used in the present invention thus have a number of unsaturations, expressed per triglyceride molecule, advantageously between 0 and 18. In these feedstocks, the degree of unsaturation, expressed as the number of unsaturations per hydrocarbon fatty chain, is advantageously between 0 and 6.

The renewable resources generally also include various impurities and especially heteroatoms such as nitrogen. The nitrogen contents in vegetable oils are generally between 1 ppm and 100 ppm by weight approximately, depending on their nature. They may be up to 1% by weight for particular feedstocks.

Said paraffinic feedstock used in the process according to the invention is advantageously produced from renewable resources according to processes known to those skilled in the art. One possible method is catalytic transformation of said renewable resources into deoxygenated paraffinic effluent in the presence of hydrogen, and in particular hydrotreatment.

Preferably, said paraffinic feedstock is produced by hydrotreatment of said renewable resources. These processes for the hydrotreatment of renewable resources are already well known and are described in numerous patents. By way of example, said paraffinic feedstock used in the process according to the invention may advantageously be produced, preferably by hydrotreatment and then by gas/liquid separation, from said renewable resources as in patent FR 2 910 483 or in patent FR 2 950 895.

Said paraffinic feedstock used in the process according to the invention may also be a paraffinic feedstock produced via a process involving a step of upgrading via the Fischer-Tropsch route. In the Fischer-Tropsch process, synthesis gas ($CO+H_2$) is converted catalytically into oxygenated products and into essentially linear hydrocarbons in gaseous, liquid or solid form. Said products obtained constitute the feedstock of the process according to the invention. Synthesis gas ($CO+H_2$) is advantageously produced from natural gas, coal, biomass, any source of hydrocarbon-based compounds or a mixture of these sources. Thus, the paraffinic feedstocks obtained, according to a Fischer-Tropsch synthetic process, from a synthesis gas ($CO+H_2$) produced from renewable resources, natural gas or coal may be used in the process according to the invention. Preferably, said paraffinic feedstock produced by Fischer-Tropsch synthesis and used in the process according to the invention predominantly comprises n-paraffins. Thus, said feedstock comprises a content of n-paraffins of greater than 60% by weight relative to the total mass of said feedstock. Said feedstock may also comprise a content of oxygenated products preferably of less than 10% by weight, a content of unsaturated substances, that is to say preferably olefinic products, preferably of less than 20% by weight, and a content of isoparaffins preferably of less than 10% by weight relative to the total mass of said feedstock.

Very preferably, said feedstock comprises a content of n-paraffins of greater than 70% by weight and even more preferably greater than 80% by weight relative to the total mass of said feedstock. The paraffins of said paraffinic feedstock contain between 9 and 25 carbon atoms, preferably between 10 and 25 and very preferably between 10 and 22.

Preferably, said paraffinic feedstock produced by Fischer-Tropsch synthesis is free of heteroatomic impurities, for instance sulfur, nitrogen or metals.

Said isomerization process is generally performed according to the following operating conditions:
- a temperature of from 200° C. to 500° C., preferably from 210° C. to 450° C. and even more preferably from 220° C. to 430° C.;
- a partial pressure of hydrogen of from 0.3 to 5.5 MPa, preferably from 0.4 to 4.8 MPa;
- a total pressure of from 0.45 to 7 MPa, preferably from 0.6 to 6 MPa; and
- a feed space velocity, expressed in kg of feedstock introduced per kilogram of catalyst and per hour, of from 0.25 to 30 $h^{-1}$, preferably from 1 to 10 $h^{-1}$ and even more preferably from 2 to 6 $h^{-1}$.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 17/61.691, filed Dec. 6, 2017, are incorporated by reference herein.

The examples that follow illustrate the invention without, however, limiting its scope.

EXAMPLES

Example 1: Synthesis of Zeolite IZM-2

Zeolite IZM-2 was synthesized in accordance with the teaching of patent FR 2 918 050 B. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 $SiO_2$; 0.0060 $Al_2O_3$; 0.1666 $Na_2O$; 0.1666 1,6-bis(methylpiperidinium)hexane; 33.3333 $H_2O$. The mixture is stirred vigorously for 30 minutes. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The solid is then introduced into a muffle furnace and calcined so as to remove the structuring agent. The calcination cycle comprises a temperature rise up to 200° C., a stage of two hours at this temperature, a temperature rise up to 550° C., followed by a stage of eight hours at this temperature and finally a return to room temperature. The temperature rises are performed at a rate of 2° C./minute. The solid thus obtained is then refluxed for 2 hours in aqueous ammonium nitrate solution (10 ml of solution per gram of solid, ammonium nitrate concentration of 3M) so as to exchange the sodium alkaline cations with ammonium ions. This refluxing step is performed four times with fresh ammonium nitrate solution, and the solid is then filtered off, washed with deionized water and dried in an oven overnight at 100° C. Finally, to obtain the zeolite in its acid (protonated $H^+$) form, a step of calcination is performed at 550° C. for 10 hours (temperature increase rate of 2° C./minute) in a traversed bed under dry air (2 normal litres per hour and per gram of solid). The solid thus obtained was analysed by x-ray diffraction and identified as being constituted by zeolite IZM-2. Characterizations via the $^{27}Al$ NMR, x-ray fluorescence and ICP methods afford the following results for IZM-2:

weight percentage of hexacoordinate aluminium atoms $Al^{VI}$: 5%, ratio of the number of moles of silicon divided by the number of moles of network aluminium, in mol/mol, Si/Al: 72, ratio of the number of moles of sodium divided by the number of moles of network aluminium, in mol/mol, Na/Al: 0.03.

Example 2: Preparation of the IZM-2/Alumina Support

The IZM-2/alumina support is obtained by blending and extrusion of the zeolite IZM-2 prepared in Example 1 with a GA7001 alumina gel provided by the company Axens. The blended paste is extruded through a trilobal die 1.8 mm in diameter. After drying in an oven overnight at 110° C., the extrudates are calcined at 500° C. for two hours (temperature increase rate of 5° C./minute) in a traversed bed under dry air (2 normal litres per hour and per gram of solid). The weight content of zeolite IZM-2 on the support after calcination is 25% by weight.

Example 3 (in Accordance with the Invention): Preparation of the Isomerization Catalyst A Catalyst A is a catalyst comprising a zeolite IZM-2, platinum and an alumina matrix. This catalyst is prepared by excess impregnation of the IZM-2/alumina support described in Example 2 with an aqueous solution containing platinum tetramine chloride $Pt(NH_3)_4Cl_2$ and ammonium nitrate $NH_4NO_3$. The mole ratio between the ammonium nitrate and the platinum is 120. The concentration of platinum tetramine chloride in the solution is $1.54 \times 10^{-3}$ mol/l and the ammonium nitrate concentration is $1.84 \times 10^{-1}$ mol/l.

20 g of support are used, the pore volume of which is filled with distilled water and the solid is left to mature for one hour at room temperature. The solid is then immersed in 160 ml of the impregnation solution described previously in a conical flask, and the whole is then stirred on a stirring table (100 rpm) at room temperature for 24 hours. The impregnation solution is then removed and the solid is rinsed with 320 ml of distilled water. The solid is then dried in a ventilated oven overnight at 110° C. and, finally, a calcination step is performed under a flow of dry air (2 normal litres per hour and per gram of solid) in a tubular oven under the following conditions:

temperature rise from room temperature to 500° C. at 5° C./min;

stage of two hours at 500° C.;

decrease to room temperature.

The Pt content measured by XRF on the calcined catalyst is 0.19% by weight, its dispersion measured by $H_2/O_2$ assay is 81%, and its coefficient of distribution measured by Castaing microprobe is 0.98. Local analyses on the catalyst examined by transmission electron microscopy are performed on various zones in the alumina matrix and on various agglomerates of IZM-2 crystallites.

FIG. 1 represents the change in the local percentage of platinum as a function of the weight % $Al_2O_3$/(weight % $Al_2O_3$+weight % IZM-2) local ratio obtained by Castaing microprobe. Locally, the weight percentage of Pt decreases as the amount of alumina increases relative to the amount of IZM-2, which reflects preferential deposition of the platinum on the zeolite IZM-2. It is thus observed that, for weight % $Al_2O_3$/(weight % $Al_2O_3$+weight % IZM-2) ratios which tend toward 1, i.e. for analysed zones not containing any zeolite IZM-2, the weight % of platinum tends toward a zero value.

Example 4 (in Accordance with the Invention): Preparation of the Isomerization Catalyst B Catalyst B is a catalyst comprising a zeolite IZM-2, platinum and an alumina matrix. This catalyst is prepared by excess impregnation of the IZM-2/alumina support prepared in Example 2 with an aqueous solution containing platinum tetramine chloride $Pt(NH_3)_4Cl_2$ and ammonium nitrate $NH_4NO_3$. The mole ratio between the ammonium nitrate and the platinum is 120. The concentration of platinum tetramine chloride in the solution is $9.62 \times 10^4$ mol/l and the ammonium nitrate concentration is $1.15 \times 10^{-1}$ mol/l.

20 g of support are used, the pore volume of which is filled with distilled water and the solid is left to mature for one hour at room temperature. The solid is then immersed in 160 ml of the impregnation solution described previously in a conical flask, and the whole is then stirred on a stirring table (100 rpm) at room temperature for 24 hours. The impregnation solution is then removed and the solid is rinsed with 320 ml of distilled water. The solid is then dried in a ventilated oven overnight at 110° C. and, finally, a calcination step is performed under a flow of dry air (2 normal litres per hour and per gram of solid) in a tubular oven under the following conditions:

temperature rise from room temperature to 500° C. at 5° C./min;

stage of two hours at 500° C.;

decrease to room temperature.

The Pt content measured by XRF on the calcined catalyst is 0.14% by weight, its dispersion measured by $H_2/O_2$ assay is 76%, and its coefficient of distribution measured by Castaing microprobe is 0.98.

FIG. 2 represents the change in the local percentage of platinum as a function of the weight % $Al_2O_3$/(weight % $Al_2O_3$+weight % IZM-2) local ratio obtained by Castaing microprobe. As for catalyst A, it is noted that, locally, the weight percentage of Pt decreases as the amount of alumina increases relative to the amount of IZM-2, which reflects preferential deposition of the platinum on the zeolite IZM-2.

Example 5 (not in Accordance with the Invention): Preparation of the Isomerization Catalyst C Catalyst C is a catalyst comprising a zeolite IZM-2, platinum and an alumina matrix. This catalyst is prepared by dry impregnation of the IZM-2/alumina support prepared in Example 2 with an aqueous solution containing platinum tetramine chloride $Pt(NH_3)_4Cl_2$. There is no ammonium salt in the impregnation solution. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (2 normal litres per hour and per gram of solid) in a tubular oven under the following conditions:
- temperature rise from room temperature to 500° C. at 5° C./min;
- stage of two hours at 500° C.;
- decrease to room temperature.

The Pt content measured by XRF on the calcined catalyst is 0.2% by weight, its dispersion measured by $H_2/O_2$ assay is 38%, and its coefficient of distribution measured by Castaing microprobe is 0.62. The Pt is thus not homogeneously distributed in the support. The non-homogeneity of distribution of the Pt on the support does not allow use of the Castaing microprobe to determine the localization of the Pt on the support. However, the analyses of the catalyst by scanning transmission electron microscopy on a Jeol JEM2100F machine, combined with a wide-angle annular detector (Stem-Haadf), reveal the localization of the platinum particles on the zeolite IZM-2 crystallites.

Example 6 (not in Accordance with the Invention): Preparation of the Isomerization Catalyst D Catalyst D is a catalyst comprising a zeolite IZM-2, platinum and an alumina matrix. This catalyst is prepared by excess impregnation of the IZM-2/alumina support prepared in Example 2 with an aqueous solution containing hexachloroplatinic acid. The concentration of hexachloroplatinic acid in the solution is $2.55 \times 10^{-3}$ mol/l.

20 g of support are used, the pore volume of which is filled with distilled water and the solid is left to mature for one hour at room temperature. The solid is then immersed in 80 ml of a hydrochloric acid HCl solution of concentration $3.52 \times 10^{-1}$ mol/l in a conical flask, and the whole is then stirred on a stirring table (100 rpm) at room temperature for one hour. The hydrochloric acid solution is then removed and the solid is immersed in 80 ml of the hexachloroplatinic acid solution described previously, and the whole is then stirred on a stirring table (100 rpm) at room temperature for 24 hours. The impregnation solution is then removed and the solid is rinsed with 160 ml of distilled water. The solid is then dried in a ventilated oven overnight at 110° C. and, finally, a calcination step is performed under a flow of dry air (2 normal litres per hour and per gram of solid) in a tubular oven under the following conditions:
- temperature rise from room temperature to 500° C. at 5° C./min;
- stage of two hours at 500° C.;
- decrease to room temperature.

The Pt content measured by XRF on the calcined catalyst is 0.20% by weight, its dispersion measured by $H_2/O_2$ assay is 83%, and its coefficient of distribution measured by Castaing microprobe is 0.95. FIG. 3 represents the change in the local weight percentage of platinum as a function of the weight % $Al_2O_3$/(weight % $Al_2O_3$+weight % IZM-2) local ratio obtained by Castaing microprobe. In contrast with catalysts A and B, it is noted that, locally, the weight percentage of Pt increases as the amount of alumina increases relative to the amount of IZM-2, which reflects preferential deposition of the platinum on the alumina.

Example 7 (not in Accordance with the Invention): Preparation of the Isomerization Catalyst E Catalyst E is a catalyst comprising a zeolite IZM-2, platinum and an alumina matrix. This catalyst is prepared by excess impregnation of the IZM-2/alumina support prepared in Example 2 with an aqueous solution containing hexachloroplatinic acid. The concentration of hexachloroplatinic acid in the solution is $1.28 \times 10^{-3}$ mol/l.

20 g of support are used, the pore volume of which is filled with distilled water and the solid is left to mature for one hour at room temperature. The solid is then immersed in 80 ml of a hydrochloric acid HCl solution of concentration $3.52 \times 10^{-1}$ mol/l in a conical flask, and the whole is then stirred on a stirring table (100 rpm) at room temperature for one hour. The hydrochloric acid solution is then removed and the solid is immersed in 80 ml of the hexachloroplatinic acid solution described previously, and the whole is then stirred on a stirring table (100 rpm) at room temperature for 24 hours. The impregnation solution is then removed and the solid is rinsed with 160 ml of distilled water. The solid is then dried in a ventilated oven overnight at 110° C. and, finally, a calcination step is performed under a flow of dry air (2 normal litres per hour and per gram of solid) in a tubular oven under the following conditions:
- temperature rise from room temperature to 500° C. at 5° C./min;
- stage of two hours at 500° C.;
- decrease to room temperature.

The Pt content measured by XRF on the calcined catalyst is 0.10% by weight, its dispersion measured by $H_2/O_2$ assay is 80%, and its coefficient of distribution measured by Castaing microprobe is 1.02.

FIG. 4 represents the change in the local weight percentage of platinum as a function of the weight % $Al_2O_3$/(weight % $Al_2O_3$+weight % IZM-2) local ratio obtained by Castaing microprobe. As for catalyst D, it is noted that, locally, the weight percentage of Pt increases as the amount of alumina increases relative to the amount of IZM-2, which reflects preferential deposition of the platinum on the alumina.

Example 8: Evaluation of the Catalytic Properties of Catalysts A and B in Accordance with the Invention and C, D and E not in Accordance with the Invention, in the Isomerization of a Paraffinic Feedstock The catalysts were tested in the isomerization of a paraffinic feedstock composed of n-hexadecane. The tests were performed in a micro-unit using a fixed-bed reactor and working in a descending stream without recycling. The analysis of the hydrocarbon-based effluents is performed online by gas chromatography. Once charged into the unit, the catalyst undergoes a first step of drying under nitrogen under the following conditions:
- nitrogen flow rate: 2 normal litres per hour and per gram of catalyst,
- total pressure: 0.1 MPa,
- temperature increase rate from room temperature to 150° C.: 5° C./min,
- stage at 150° C. for 30 minutes.

After drying, the nitrogen is replaced with hydrogen and a step of reduction under a flow of pure hydrogen is then performed under the following conditions:
- hydrogen flow rate: 5 normal litres per hour and per gram of catalyst,
- total pressure: 1.1 MPa,
- temperature increase rate from 150 to 450° C.: 5° C./min,
- stage at 450° C. for 1 hour.

After the reduction step, the temperature is reduced to 230° C. and the catalyst is placed in contact with n-hexadecane under the following conditions:
- feed space velocity of 2 g of n-hexadecane per hour and per gram of catalyst,
- mole ratio of hydrogen to n-hexadecane of 10,
- total pressure of 1.1 MPa.

The conversion is modified by varying the temperature; and at each temperature stage, two analyses of the effluent are performed, which makes it possible to calculate the catalytic performance and to check the stability of the catalytic performance for said temperature stage. Typically, the temperature is varied between 230 and 350° C. in temperature stages of 5° C. The analysis of the effluents is performed integrally by means of an online GC system. The temperature required to reach 50% conversion serves as a descriptor of the activity of the catalyst, while the maximum yield of hexadecane isomers obtained serves as a descriptor of the isomerizing properties of the catalyst.

Table 1 thus reports the catalytic performance of the catalysts in the hydroconversion of n-hexadecane. It is observed that the catalysts in accordance A and B prepared according to the process of the invention have markedly higher activity than the catalysts not in accordance with the invention: conversion of 50% of the n-hexadecane is obtained for temperatures typically 13 to 15° C. lower than for the catalysts not in accordance D and E, and typically 21 to 22° C. lower than for catalyst C. Furthermore, catalysts A and B in accordance with the invention make it possible to achieve the highest maximum yields of n-hexadecane isomers. Catalysts A and B prepared according to the process of the invention thus have both the best activities and the best isomerizing properties.

TABLE 1 catalytic performance of catalysts A, B, C, D and E in the hydroconversion of n-hexadecane

| | Catalyst | | | | |
|---|---|---|---|---|---|
| | A (in accordance) | B (in accordance) | C (not in accordance) | D (not in accordance) | E (not in accordance) |
| Temperature at 50% conversion (° C.) | 254 | 255 | 276 | 269 | 268 |
| Max yield of isomers (weight %) | 87 | 87 | 86 | 84 | 85 |

BRIEF DESCRIPTION OF THE DRAWINGS

FIG. 1 shows the change in the local weight % as a function of the weight % $Al_2O_3$/(weight % $Al_2O_3$+weight % IZM-2) local ratio for catalyst A in accordance with the invention.

FIG. 2 shows the change in the local weight % as a function of the weight % $Al_2O_3$/(weight % $Al_2O_3$+weight % IZM-2) local ratio for catalyst B in accordance with the invention.

FIG. 3 shows the change in the local weight % as a function of the weight % $Al_2O_3$/(weight % $Al_2O_3$+weight % IZM-2) local ratio for catalyst D not in accordance with the invention.

FIG. 4 shows the change in the local weight % as a function of the weight % $Al_2O_3$/(weight % $Al_2O_3$+weight % IZM-2) local ratio for catalyst E not in accordance with the invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process preparing a difunctional catalyst comprising an acid function from zeolite IZM-2, a hydrogenating function from at least one platinum or palladium noble metal from group VIII of the Periodic Table, and a matrix, said process comprising at least the following:
   i) preparing the support for the catalyst by forming zeolite IZM-2 with a matrix,
   ii) depositing at least one noble metal from group VIII of the Periodic Table by impregnation of the support prepared in i) with an aqueous solution comprising
      at least one ammoniacal compound that is a platinum (II) tetramine salt of formula $Pt(NH_3)_4(OH)_2$, $Pt(NH_3)_4(NO_3)_2$ or $Pt(NH_3)_4X_2$, a platinum(IV) hexamine salt of formula $Pt(NH_3)_6X_4$; a platinum(IV) halopentamine salt of formula $(PtX(NH_3)_5)X_3$; a platinum N-tetrahalodiamine salt of formula $PtX_4(NH_3)_2$; a halogenated compound of formula $H(Pt(acac)_2X)$; or a palladium(II) salt of formula $Pd(NH_3)_4SO_4$ or $Pd(NH_3)_4X_2$, wherein X is chlorine, fluorine, bromine or iodine, and "acac" is an acetylacetonate group,
      and at least one ammonium salt that is ammonium nitrate $NH_4NO_3$, ammonium chloride $NH_4Cl$, ammonium hydroxide $NH_4OH$, ammonium bicarbonate $NH_4HCO_3$, ammonium acetate $NH_4H_3C_2O_2$, or a mixture thereof,
      the mole ratio between the ammonium salt and the noble metal being 0.1 to 400.

2. The process according to claim 1, in which i) is performed by blending-extrusion.

3. The process according to claim 1, in which said matrix used in i) is alumina.

4. The process according to claim 1, in which the support obtained on conclusion of i) is subjected to drying performed at a temperature of 50 to 180° C.

5. The process according to claim 1, in which X is chlorine.

6. The process according to claim 1, in which the impregnation of the support in ii) is performed via "dry" impregnation or excess impregnation of said solution.

7. The process according to claim 1, in which the aqueous solution from ii) comprises a platinum(II) tetramine salt of formula $Pt(NH_3)_4(OH)_2$, $Pt(NH_3)_4(NO_3)$ or $Pt(NH_3)_4X_2$, a platinum(IV)hexamine salt of formula $Pt(NH_3)_6X_4$; a platinum(IV) halopentamine salt of formula $(PtX(NH_3)_5)X_3$; a platinum N-tetrahalodiamine salt of formula $PtX_4(NH_3)_2$; or a halogenated compound of formula $H(Pt(acac)_2X)$; X and "acac" having the abovementioned meaning.

8. The process according to claim 7, in which said solution comprises a platinum(II) tetramine salt of formula $Pt(NH_3)_4(OH)_2$, $Pt(NH_3)_4(NO_3)$ or $Pt(NH_3)_4X_2$.

9. The process according to claim 1, in which the aqueous solution from ii) further comprises precursors of metals from groups IIIA, IVA or VIIB of the Periodic Table of the Elements that are gallium, indium, tin or rhenium.

10. The process according to claim 1, in which the ammonium salt and the noble metal have a mole ratio of 0.3 to 150 in the solution from ii).

11. The process according to claim 1, wherein in (ii) the support is subsequently impregnated with a solution comprising precursors of metals from groups IIIA, IVA and or VIIB of the Periodic Table of the Elements that are gallium, indium, tin or rhenium.

* * * * *